United States Patent
Hartley et al.

(10) Patent No.: US 10,195,059 B2
(45) Date of Patent: Feb. 5, 2019

(54) COMPOSITE STENT GRAFT

(71) Applicant: Cook Medical Technologies LLC, Bloomington, IN (US)

(72) Inventors: David Ernest Hartley, Wannanup (AU); Michael Lawrence-Brown, City Beach (AU)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 15/804,634

(22) Filed: Nov. 6, 2017

(65) Prior Publication Data

US 2018/0055667 A1    Mar. 1, 2018

Related U.S. Application Data

(60) Continuation of application No. 14/287,964, filed on May 27, 2014, now Pat. No. 9,943,422, which is a
(Continued)

(51) Int. Cl.
*A61F 2/852*      (2013.01)
*A61F 2/07*      (2013.01)
(Continued)

(52) U.S. Cl.
CPC ............... *A61F 2/852* (2013.01); *A61F 2/07* (2013.01); *A61F 2/958* (2013.01); *A61F 2/89* (2013.01);
(Continued)

(58) Field of Classification Search
CPC ................. A61F 2/07; A61F 2002/821; A61F 2002/075; A61F 2002/061
See application file for complete search history.

(56) References Cited

U.S. PATENT DOCUMENTS

| 4,902,508 A | 2/1990 | Badylak et al. |
| 5,383,892 A | 1/1995 | Cardon et al. |

(Continued)

FOREIGN PATENT DOCUMENTS

| WO | WO 98/22158 A1 | 5/1998 |
| WO | WO 98/53761 A1 | 12/1998 |

(Continued)

OTHER PUBLICATIONS

International Search Report for corresponding PCT/US2004/033567 dated Jul. 2, 2005 (4 pages).
(Continued)

*Primary Examiner* — Julie A Szpira
(74) *Attorney, Agent, or Firm* — Brinks Gilson & Lione (57) ABSTRACT

A composite stent graft has a balloon expandable stent portion, a tubular graft material portion inside or outside of the balloon expandable stent portion and self expanding stents associated with the tubular graft material portion. Part of the balloon expandable stent portion can extend beyond the proximal end of the tubular graft material portion. The tubular graft material can be polytetrafluoroethylene, dacron, polyamide, sub intestinal mucosa or any other suitable biocompatible material. A method of deploying which includes flaring a part of the balloon expandable stent portion is also discussed.

10 Claims, 5 Drawing Sheets

Related U.S. Application Data division of application No. 10/962,766, filed on Oct. 12, 2004, now Pat. No. 8,734,501.

(60) Provisional application No. 60/510,259, filed on Oct. 10, 2003.

(51) Int. Cl.
*A61F 2/958* (2013.01)
*A61F 2/91* (2013.01)
*A61F 2/954* (2013.01)
*A61F 2/06* (2013.01)
*A61F 2/82* (2013.01)
*A61F 2/89* (2013.01)
*A61F 2/915* (2013.01)

(52) U.S. Cl.
CPC ............... *A61F 2/91* (2013.01); *A61F 2/915* (2013.01); *A61F 2/954* (2013.01); *A61F 2002/061* (2013.01); *A61F 2002/075* (2013.01); *A61F 2002/821* (2013.01); *A61F 2250/0039* (2013.01)

(56) References Cited

U.S. PATENT DOCUMENTS

| | | |
|---|---|---|
| 5,387,235 A | 2/1995 | Chuter |
| 5,632,762 A | 5/1997 | Myler |
| 5,711,969 A | 1/1998 | Patel et al. |
| 5,720,776 A | 2/1998 | Chuter et al. |
| 5,733,337 A | 3/1998 | Carr, Jr. et al. |
| 5,817,126 A | 10/1998 | Imran |
| 5,885,619 A | 3/1999 | Patel et al. |
| 5,955,110 A | 9/1999 | Patel et al. |
| 5,968,096 A | 10/1999 | Whitson et al. |
| 5,984,955 A | 11/1999 | Wisselink |
| 6,168,621 B1 | 1/2001 | Vrba |
| 6,206,931 B1 | 3/2001 | Cook et al. |
| 6,293,955 B1 | 9/2001 | Houser et al. |
| 6,325,820 B1 | 12/2001 | Khosravi et al. |
| 6,699,277 B1* | 3/2004 | Freidberg ............... A61F 2/07 623/1.13 |
| 6,911,040 B2 | 6/2005 | Johnson et al. |
| 6,964,681 B2 | 11/2005 | Murray, III et al. |
| 7,175,652 B2 | 2/2007 | Cook et al. |
| 2001/0016766 A1* | 8/2001 | Vardi ....................... A61F 2/82 623/1.11 |
| 2001/0053929 A1 | 12/2001 | Vonesh et al. |
| 2002/0198587 A1* | 12/2002 | Greenberg ............... A61F 2/07 623/1.13 |
| 2002/0198588 A1 | 12/2002 | Armstrong et al. |
| 2003/0120332 A1 | 6/2003 | Hartley |
| 2003/0195609 A1 | 10/2003 | Berenstein et al. |
| 2004/0054396 A1 | 3/2004 | Hartley et al. |
| 2004/0073289 A1 | 4/2004 | Hartley |
| 2004/0082990 A1 | 4/2004 | Hartley |
| 2004/0098079 A1 | 5/2004 | Hartley et al. |
| 2004/0106978 A1 | 6/2004 | Greenberg et al. |
| 2006/0241740 A1 | 10/2006 | Vardi et al. |

FOREIGN PATENT DOCUMENTS

| | | |
|---|---|---|
| WO | WO 99/29262 A1 | 6/1999 |
| WO | WO 02/30329 A2 | 4/2002 |
| WO | WO 03/034948 A1 | 5/2003 |
| WO | WO 03/053287 A1 | 7/2003 |
| WO | WO 03/063729 A2 | 8/2003 |
| WO | WO 03/082153 A2 | 10/2003 |
| WO | WO 2004/002365 A1 | 1/2004 |
| WO | WO 2004/002370 A1 | 1/2004 |
| WO | WO 2004/017867 A1 | 3/2004 |
| WO | WO 2004/028399 A2 | 4/2004 |

OTHER PUBLICATIONS

European Patent Office Communication for corresponding EP 04 794819.5 dated Jun. 20, 2013 (5 pages).
European Patent Office Communication for corresponding EP 04794819.5 dated Dec. 17, 2014 (4 pages).
European Patent Office Communication for corresponding EP 04794819.5 dated Apr. 9, 2014 (5 pages).

* cited by examiner

COMPOSITE STENT GRAFT

RELATED APPLICATIONS

This application is a continuation of U.S. application Ser. No. 14/287,964, filed May 27, 2014, which is a divisional of U.S. application Ser. No. 10/962,766, filed Oct. 12, 2004, now U.S. Pat. No. 8,734,501, which claims the benefit of the filing date under 35 U.S.C. § 119(e) of Provisional U.S. Patent Application Ser. No. 60/510,259, filed Oct. 10, 2003. All of the foregoing applications are hereby incorporated by reference in their entireties.

BACKGROUND

1. Field of the Invention

This invention relates to a stent graft for use in the human or animal body and more particularly to a stent graft which can be used as a side branch stent graft from a main vessel stent graft.

2. Background of the Invention

There is a problem with the deployment of a branch stent graft from a main stent graft into a side artery for instance. If a branch stent graft is made substantially flexible, that is, for instance, manufactured with all self expanding stents, then there is a danger that, where a graft extends from a main graft through an aneurised space within, for instance an aneurised aorta and then into a side branch artery, such as a renal artery, as the main graft moves the side branch can kink which can close off the lumen through the branch stent graft.

If, however, an essentially rigid stent graft such as a balloon expandable graft is used then the distal end of the stent graft can cause significant distortion of the side branch vessel and there can be a considerable problem with fibrosis, stenosis or damage to the side branch artery at the distal end of the stent graft.

Applicant has found that this problem can be solved by providing greater flexibility of the branch stent graft within the side branch but having a degree of rigidity in the main vessel region.

There is also a problem with holding the branch stent graft into a fenestration in a main graft and this present invention proposes ways to satisfy this requirement.

There can also be problems with stenosis at the distal end of the side graft and this invention proposes methods by which ingrowth at the end of a balloon expandable stent can be reduced.

BRIEF SUMMARY

In one form, therefore, the invention is said to reside in a composite stent graft having a tubular body with a lumen therethrough, the tubular body comprising a balloon expandable stent portion, a tubular graft material portion disposed inside or outside of the balloon expandable stent portion and extending from the balloon expandable stent portion at one end thereof and self expanding stents associated with the tubular graft material portion disposed at least in the tubular graft material portion extending from the balloon expandable stent portion.

It will be seen that by this invention there is provided an arrangement by which the balloon expandable stent portion which is substantially rigid can extend from a main graft across an aneurised space to the side branch artery or vessel and then within the side branch artery the device has self expanding stents disposed within or outside the tubular graft material which provide a degree of flexibility to reduce the incidence of stenosis or fibrosis.

Preferably, there is a portion of the balloon expandable stent portion which extends beyond the proximal end of the tubular graft material portion. This extension portion allows for expansion of the balloon expandable stent beyond the diameter of the tubular graft material in that extension portion. This enables the extension portion of the balloon expandable stent to be flared to enable it to be connected into a fenestration in a main graft so that it is securely received in it.

The tubular graft material can include polytetrafluoroethylene, dacron, polyamide or any other suitable biocompatible graft material.

While DACRON, expanded polytetrafluoroethylene (ePTFE), or other synthetic biocompatible materials can be used for the tubular graft material for the stent graft, a naturally occurring biomaterial, such as collagen, is highly desirable, particularly a specially derived collagen material known as an extracellular matrix (ECM), such as small intestinal submucosa (SIS). Besides SIS, examples of ECM's include pericardium, stomach submucosa, liver basement membrane, urinary bladder submucosa, tissue mucosa, and dura mater.

SIS is particularly useful, and can be made in the fashion described in Badylak et al., U.S. Pat. No. 4,902,508; Intestinal Collagen Layer described in U.S. Pat. No. 5,733,337 to Carr and in 17 Nature Biotechnology 1083 (November 1999); Cook et al., WIPO Publication WO 98/22158, dated 28 May 1998, which is the published application of PCT/US97/14855, the teachings of which are incorporated herein by reference. Irrespective of the origin of the material (synthetic versus naturally occurring), the material can be made thicker by making multilaminate constructs, for example SIS constructs as described in U.S. Pat. Nos. 5,968,096; 5,955,110; 5,885,619; and 5,711,969. In addition to xenogenic biomaterials, such as SIS, autologous tissue can be harvested as well, for use in forming the tubular graft material. Additionally Elastin or Elastin-Like Polypetides (ELPs) and the like offer potential as a material to fabricate the tubular graft material to form a device with exceptional biocompatibility.

SIS is available from Cook Biotech, West Lafayette, Ind., USA.

The self expanding stent can include Nitinol™, stainless steel or any other suitable material.

The balloon expandable stent portion can include a shape memory material such as titanium, magnesium, nickel, alloys and the like.

When the tubular graft material is disposed inside the balloon expandable portion the portion of the self expanding stents extending into the balloon expandable portion will assist to hold the tubular graft material against the balloon expandable stent portion. Stitching can be provided to retain the tubular graft material to each of the self expanding stents and the balloon expanding stents.

The self expanding stents can be provided either inside or outside the tubular graft material. For instance they can be provided outside along part of the length and inside at the distal end so that the outside surface of the tubular graft material provides a good seal against the wall of the branch artery or vessel when deployed.

In a further form the invention can be said to reside in a stent graft having tubular body with a lumen therethrough, a first portion at one end of the tubular body that can be flared to retain the stent in a fenestration in another stent graft positioned in a main vessel, a second relatively rigid central portion that can bridge from the fenestration to a branch vessel of the main vessel and a third relatively flexible portion that can extend into a branch vessel to conform thereto.

Preferably the second and third portions include a covering or lining of biocompatible graft material.

In a preferred embodiment of the invention the first and second portions comprise or include a balloon expandable stent. The third portion may comprise or include self expanding stents.

In a further form the invention comprises a composite stent graft comprising a biocompatible graft material tube, a balloon expandable stent disposed inside or outside a first part of the graft material tube and extending from the graft material tube at one end thereof and at least one self expanding stent associated with a second part of the graft material tube.

Preferably the at least one self expanding stent associated with the second part of the graft material tube comprises a plurality of external self expanding stents and at least one terminal internal self expanding stent.

In a further form the invention comprises a method of retaining a side branch stent graft into a fenestration in a main graft, the side branch stent graft having a tubular body with a lumen therethrough, a first portion at one end thereof being balloon expandable, a second relatively rigid central portion that can bridge from the fenestration and a third relatively flexible portion, the method including the steps of; deploying the side branch stent graft through the fenestration such that at least part of the first portion remains within the main stent graft; and expanding a balloon in the region of the fenestration whereby to flare that part of the first portion which is within the main stent graft, whereby to assist with retention of the side branch stent graft into the fenestration in the main graft.

Preferably the step of expanding the balloon includes the step of expanding a first balloon in the second portion to retain the position of the side branch stent graft and expanding a second balloon in the region of the fenestration whereby to flare that part of the first portion which is within the main stent graft. Preferably the first balloon is a non-compliant balloon and the second balloon is a compliant balloon.

U.S. Pat. No. 6,206,931 entitled "Graft Prosthesis Materials" discloses graft prosthesis materials and a method for implanting, transplanting, replacing and repairing a part of a patient and particularly the manufacture and use of a purified, collagen based matrix structure removed from a submucosa tissue source. These features and other features disclosed in U.S. Pat. No. 6,206,931 could be used with the present invention and the disclosure of U.S. Pat. No. 6,206,931 is herewith incorporated in its entirety into this specification.

U.S. Pat. No. 5,387,235 entitled "Expandable Transluminal Graft Prosthesis For Repair Of Aneurysm" discloses apparatus and methods of retaining grafts onto deployment devices. These features and other features disclosed in U.S. Pat. No. 5,387,235 could be used with the present invention and the disclosure of U.S. Pat. No. 5,387,235 is herewith incorporated in its entirety into this specification.

U.S. Pat. No. 5,720,776 entitled "Barb and Expandable Transluminal Graft Prosthesis For Repair of Aneurysm" discloses improved barbs with various forms of mechanical attachment to a stent. These features and other features disclosed in U.S. Pat. No. 5,720,776 could be used with the present invention and the disclosure of U.S. Pat. No. 5,720,776 is herewith incorporated in its entirety into this specification.

U.S. Pat. No. 6,206,931 entitled "Graft Prosthesis Materials" discloses graft prosthesis materials and a method for implanting, transplanting replacing and repairing a part of a patient and particularly the manufacture and use of a purified, collagen based matrix structure removed from a submucosa tissue source. These features and other features disclosed in U.S. Pat. No. 6,206,931 could be used with the present invention and the disclosure of U.S. Pat. No. 6,206,931 is herewith incorporated in its entirety into this specification.

PCT Patent Publication No. WO 98/53761 entitled "A Prosthesis And A Method And Means Of Deploying A Prosthesis" discloses an introducer for a prosthesis which retains the prosthesis so that each end can be moved independently. These features and other features disclosed in PCT Patent Publication No. WO 98/53761 could be used with the present invention and the disclosure of PCT Patent Publication No. WO 98/53761 is herewith incorporated in its entirety into this specification.

PCT Patent Publication No. WO 99/29262 entitled "Endoluminal Aortic Stents" discloses a fenestrated prosthesis for placement where there are intersecting arteries. This feature and other features disclosed in PCT Patent Publication No. WO 99/29262 could be used with the present invention and the disclosure of PCT Patent Publication No. WO 99/29262 is herewith incorporated in its entirety into this specification.

PCT Patent Publication No. WO 03/034948 entitled "Prosthesis For Curved Lumens" discloses prostheses with arrangements for bending the prosthesis for placement into curved lumens. This feature and other features disclosed in PCT Patent Publication No. WO 03/034948 could be used with the present invention and the disclosure of PCT Patent Publication No. WO 03/034948 is herewith incorporated in its entirety into this specification.

U.S. Provisional Patent Application Ser. No. 60/392,667, filed Jun. 28, 2002, and U.S. patent application Ser. No. 10/609,846, filed Jun. 30, 2003, entitled "Thoracic Deployment Device" disclose introducer devices adapted for deployment of stent grafts particularly in the thoracic arch. This feature and other features disclosed in U.S. Provisional Patent Application Ser. No. 60/392,667 and U.S. patent application Ser. No. 10/609,846, filed Jun. 30, 2003 could be used with the present invention and the disclosure of U.S. Provisional Patent Application Ser. No. 60/392,667 and U.S. patent application Ser. No. 10/609,846, filed Jun. 30, 2003 are herewith incorporated in their entirety into this specification.

U.S. Provisional Patent Application Ser. No. 60/392,599, filed Jun. 28, 2002, and U.S. patent application Ser. No. 10/609,835, filed Jun. 30, 2003, entitled "Thoracic Aortic Aneurysm Stent Graft" disclose stent grafts that are useful in treating aortic aneurysms particularly in the thoracic arch. This feature and other features disclosed in U.S. Provisional Patent Application Ser. No. 60/392,599 and U.S. patent application Ser. No. 10/609,835, filed Jun. 30, 2003 could be used with the present invention, and the disclosure are herewith incorporated in their entirety into this specification.

U.S. Provisional Patent Application Ser. No. 60/391,737, filed Jun. 26, 2002, U.S. patent application Ser. No. 10/602,930, filed Jun. 24, 2003, and PCT Patent Publication Number WO 2004/002365 entitled "Stent-Graft Fastening" disclose arrangements for fastening stents onto grafts particularly for exposed stents. This feature and other features disclosed in U.S. Provisional Patent Application No. 60/391,737, U.S. patent application Ser. No. 10/602,930, and PCT Patent Publication Number WO 2004/002365 could be used with the present invention and the disclosure of U.S. Provisional Patent Application Ser. No. 60/391,73, U.S. patent application Ser. No. 10/602,930, and PCT Patent Publication Number WO 2004/002365 are herewith incorporated in its entirety into this specification.

U.S. Provisional Patent Application Ser. No. 60/405,367, filed Aug. 23, 2002, U.S. patent application Ser. No. 10/647, 642, filed Aug. 25, 2003, and PCT Patent Publication No. WO 2004/017868 entitled "Asymmetric Stent Graft Attachment" disclose retention arrangements for retaining onto and releasing prostheses from introducer devices. This feature and other features disclosed in U.S. Provisional Patent Application Ser. No. 60/405,367, filed Aug. 23, 2002, U.S. patent application Ser. No. 10/647,642, filed Aug. 25, 2003, and PCT Patent Publication No. WO 2004/017868 could be used with the present invention and the disclosure of U.S. Provisional Patent Application Ser. No. 60/405,367, filed Aug. 23, 2002, U.S. patent application Ser. No. 10/647,642, filed Aug. 25, 2003, and PCT Patent Publication No. WO 2004/017868 are herewith incorporated in its entirety into this specification.

U.S. patent application Ser. No. 10/322,862, filed Dec. 18, 2002 and published as Publication No. US2003-0120332, and PCT Patent Publication No. WO03/053287 entitled "Stent Graft With Improved Adhesion" disclose arrangements on stent grafts for enhancing the adhesion of such stent grafts into walls of vessels in which they are deployed. This feature and other features disclosed in U.S. patent application Ser. No. 10/322,862, filed Dec. 18, 2002 and published as Publication No. US2003-0120332, and PCT Patent Publication No. WO03/053287 could be used with the present invention and the disclosure of U.S. patent application Ser. No. 10/322,862, filed Dec. 18, 2002 and published as Publication No. US2003-0120332, and PCT Patent Publication No. WO03/053287 are herewith incorporated in its entirety into this specification.

U.S. Provisional Patent Application Ser. No. 60/405,769, filed Aug. 23, 2002, U.S. patent application Ser. No. 10/645, 095, filed Aug. 23, 2003, and PCT Patent Publication Number WO 2004/017867 entitled "Composite Prostheses" discloses prostheses or stent grafts suitable for endoluminal deployment. These prostheses and other features disclosed in U.S. Provisional Patent Application Ser. No. 60/405,769, filed Aug. 23, 2002, U.S. patent application Ser. No. 10/645, 095, filed Aug. 23, 2003, and PCT Patent Publication Number WO 2004/017867, could be used with the present invention and the disclosure of U.S. Provisional Patent Application Ser. No. 60/405,769, filed Aug. 23, 2002, U.S. patent application Ser. No. 10/645,095, filed Aug. 23, 2003, and PCT Patent Publication Number WO 2004/017867 are herewith incorporated in its entirety into this specification.

This then generally describes the invention but to assist with understanding reference will now be made to the accompanying drawings which show a preferred embodiment of the invention.

DETAILED DESCRIPTION OF THE DRAWINGS AND THE PRESENTLY PREFERRED EMBODIMENTS

Figure 1:
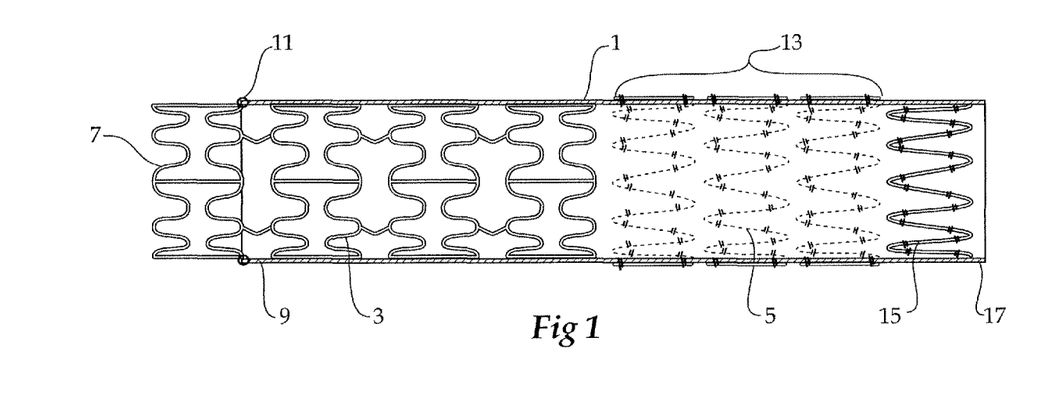
FIG. 1 shows a longitudinal cross-sectional view of a composite stent graft according to one embodiment of this invention.
Figure 2:
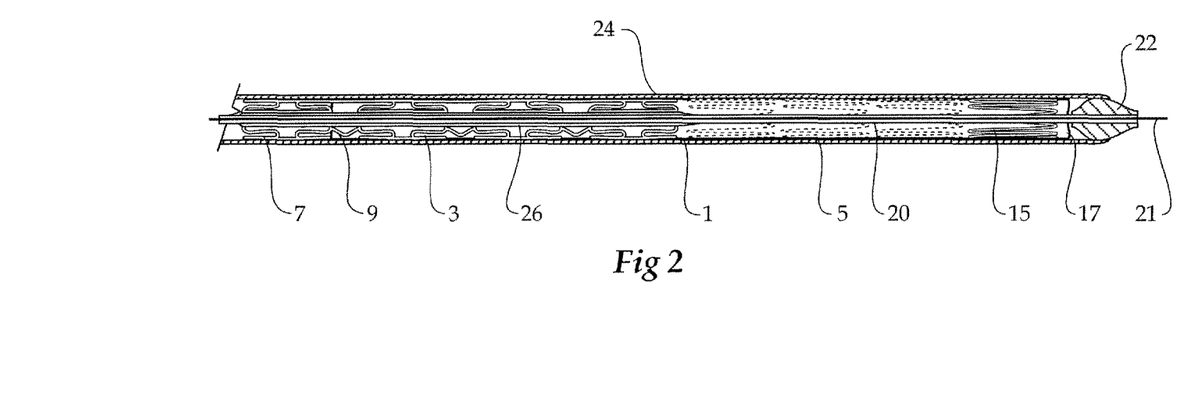
FIG. 2 shows the composite stent graft of FIG. 1 compressed and received in a deployment device.

Now looking more closely at FIGS. 1 and 2, it will be seen that the composite stent graft includes a tubular graft material 1 and within the tubular graft material there is an balloon expandable stent 3 (shown in an expanded configuration in FIG. 1 and in a radially compressed condition in FIG. 2) and a number of self expanding stents 5. The balloon expandable stent 3 has a particular configuration of struts shown but the invention is not limited to any one configuration of struts. The balloon expandable stent 3 has an extension portion 7 which extends beyond the proximal end 9 of the tubular graft material 1. The tubular graft material 1 is stitched at 11 to the balloon expandable stent. Further stitching can also be provided. The self expanding stents 5 are positioned on the outside of the tubular graft material in the region 13 and the final self expanding stent 15 is positioned on the inside of the tubular graft material 1 at the distal end 17 of the tubular graft material 1.

The extension portion 7 comprises the first portion discussed above, the remainder of the balloon expandable stent 3 comprises the second portion and the self expanding stents 5 and 5 comprise the relatively flexible portion of the composite stent graft.

The balloon expandable stent 3 may be a radially expandable surgical stent formed from a shape memory material such as a nickel-titanium alloy. The stent can include a series of wave-like struts spaced apart by gaps. Each gap can be spanned by tie bars at a maximum width portion of the gap and/or by angled links or straight links at a minimum width portion of a gap. Hence, axial expansion or contraction of the stent is avoided when the stent is radially expanded.

The self expanding stents 5 and 15 can be zig zag Gianturco style Z stents having a plurality of struts with bends between the struts and formed into a substantially cylindrical form.

FIG. 2 shows the stent graft of FIG. 1 compressed and received within a deployment device.

The deployment device includes a guide wire catheter 20 with a nose cone 22 at one end and sheath 24 covering the stent graft and holding the self expanding stents 5 and 15 in a radially compressed or collapsed condition.

On the guide wire catheter 20 is an inflatable balloon 26 which can be inflated with suitable material to expand the balloon expandable stent portion of the stent graft as required. It will be realised that in some embodiments the balloon can be provided on a separate balloon catheter deployed over the guide wire 21 after the deployment of the device as will be discussed later.

Figure 3:
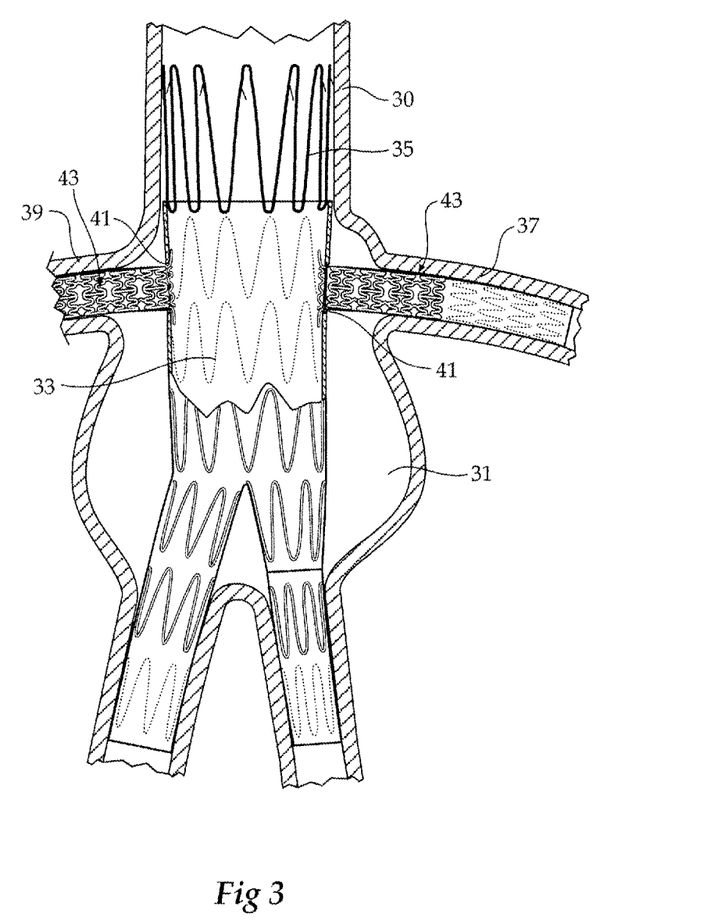
FIG. 3 shows a schematic view of deployment of side branch stent grafts from a main graft.

FIG. 3 shows a schematic view of the deployment of a main graft into a aneurysed aorta and the deployment of side branch grafts from the main graft into renal arteries. The aorta 30 has an aneurysm 31 and a main graft 33 has been deployed into the aneurised space. The main graft 33 has super-renal uncovered stent 35 which is received in a non-aneurysed region of the aorta and provides a top support for the main graft 33. The main aneurised region 31, however, extends up past the renal arteries 37 and 39 and as such is necessary to provide side branch grafts to these arteries.

For this purpose there are fenestrations 41 provided into the main graft and it is through these fenestrations that the side branch or composite stent grafts 43 are deployed as will be discussed in more detail in respect to FIGS. 4-7.

It will be noted, however, that the side branch stent grafts 43 extending from the main graft to the renal arteries 37 and 39 cross a region of aneurised region 31. If there was movement of the main graft 33 with respect to the aneurysm and if there was a non-rigid portion of stent graft in this space the lumen of the side branch graft could be closed off by kinking. The expanded balloon expandable portion of the stent graft in this region will act to prevent this occurring.

FIGS. 4-7 show the various stages in deployment of a branched stent graft from a main graft into a side branch artery for instance.

Figure 4:
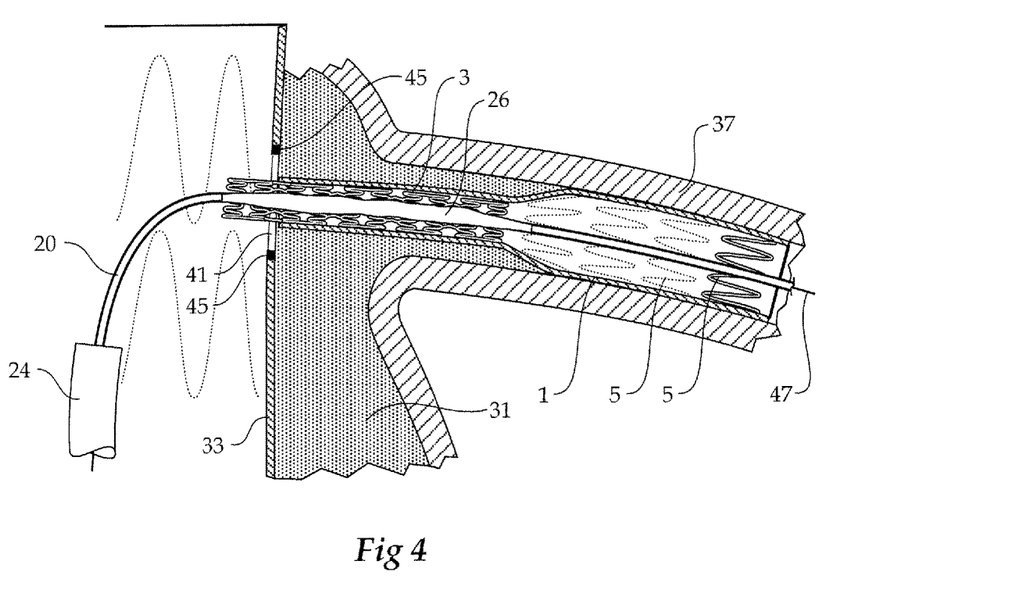
FIGS. 4 to 7 show various stages of deployment of the composite stent graft according to this invention into a side branch artery from a main graft.

As can be seen in FIG. 4 a main graft 33 has been deployed into an aorta and extends through an aneurised space 31. The main graft has a fenestration 41 with radiopaque markers 45 around its periphery which assist a surgeon in locating the fenestration with respect to the side branch artery 37 after the main graft 33 has been deployed. The side branch artery 37 has had a guide wire 47 deployed into it and a deployment catheter with the stent graft according to this invention mounted onto it of the type shown in FIG. 2 has been deployed over the guide wire 47. The sheath 24 has been withdrawn. This allows the self expanding stents 5 and 15 to expand within the side branch artery 37 so that the tubular graft material 1 is engaged against the wall of the artery.

The balloon 26, however, has not been expanded and therefore the balloon expandable stent 3 of the stent graft is not expanded.

Figure 5:
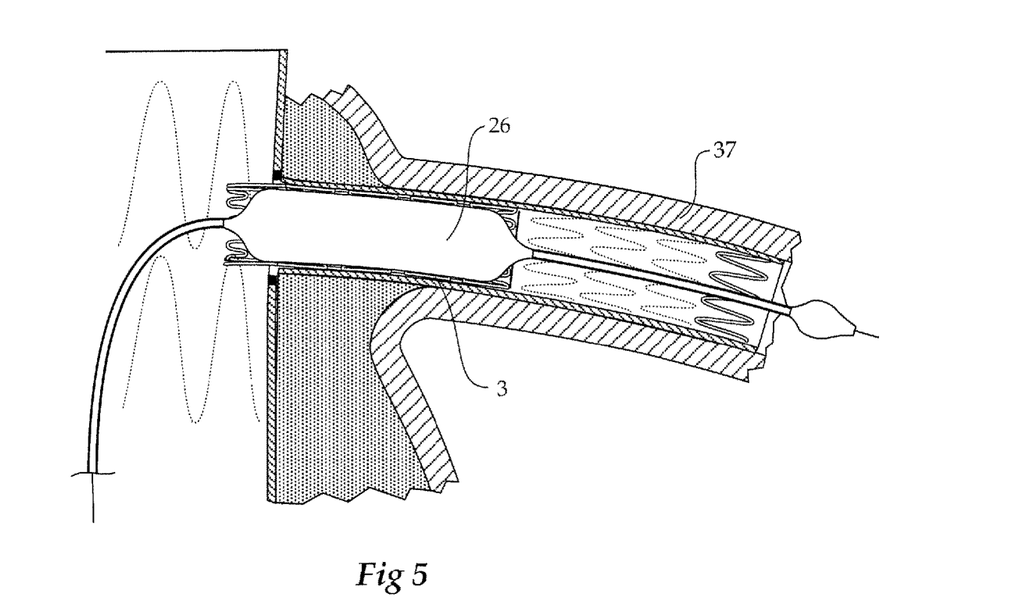

As can be seen in FIG. 5, the balloon 26 has been expanded by known means and the balloon expandable stent 3 has expanded to engage against the walls of the side branch artery 37.

The balloon 26 is then deflated and the deployment device on guide wire 20 is then removed leaving the guide wire 20 in place.

Figure 6:
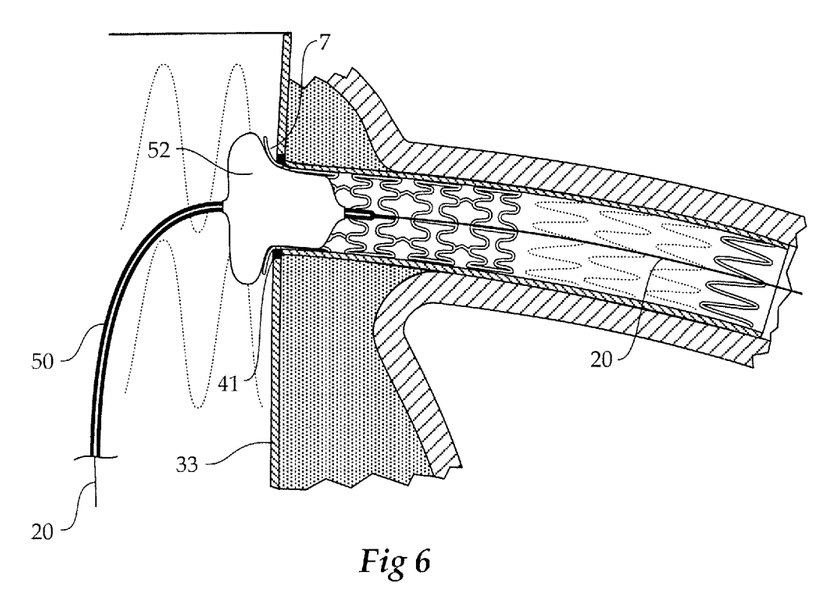

As depicted in FIG. 6, another balloon catheter 50 is then deployed over the guide wire 20 and the balloon 52 on the balloon catheter 50 is positioned so that it is partially within the proximal end of the stent graft and partially outside the stent graft in the region of the fenestration 41 and then it is expanded. Expansion causes the extension portion 7 to be flared so that the proximal end of the stent graft 7 is firmly received within the fenestration 41 of the main graft 33.

Figure 7:
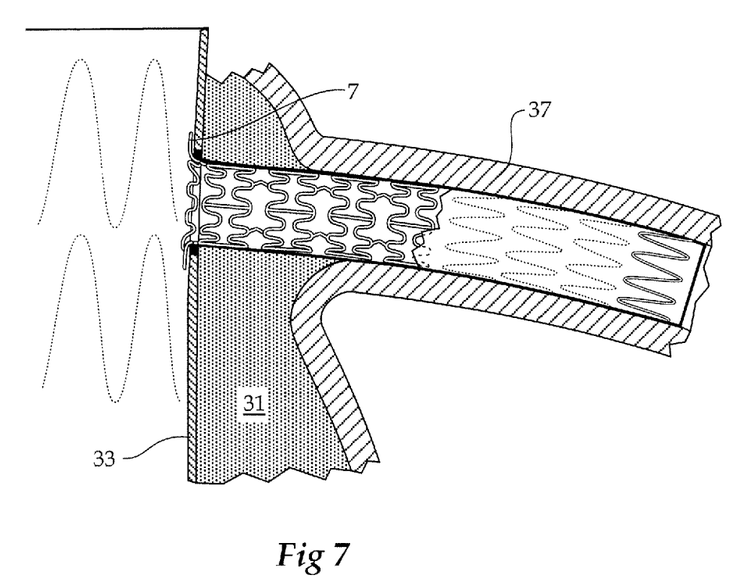

As shown in FIG. 7 the flaring can be extended to the extent that the extension portion 7 is completely flared against the inside wall of the stent graft.

A blood flow path is therefore provided from the main graft into the branch artery 37 which includes a rigid portion across the aneurised space 31 and a more flexible portion within the branch artery 37. This will assist with prevention of stenosis at the junction between the stent graft and the side branch artery.

Figure 8:
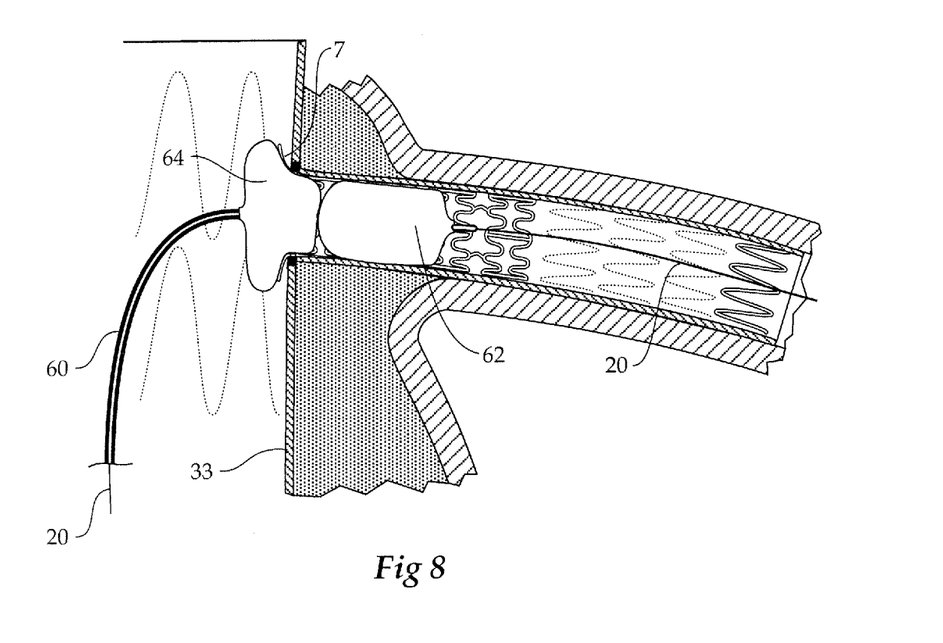
FIG. 8 shows an alternative method of expansion of part of the composite stent graft.

FIG. 8 shows an alternative method to that shown in FIG. 6 for the expansion and flaring of the extension portion 7 of the composite stent graft so that the proximal end of the stent graft 7 is firmly received within the fenestration 41 of the main graft 33.

For this method a dual balloon catheter 60 is used. The dual balloon catheter 60 has a first balloon 62 near its proximal end and a second balloon 64 just distal of the first balloon 62. Both the balloons are separately inflatable by the use of multiple lumens in the catheter. The dual balloon catheter 60 is deployed over the guide wire 20 so that the balloon 62 is fully received within the balloon expanded portion 3 of the composite stent. This balloon 62 can be used to expand the balloon expanded portion 3 as discussed in relation to FIG. 5 or can be used after the stage discussed in relation to FIG. 5 has been performed. The balloon 62 is expanded or left expanded and then the balloon 64 is expanded to cause the flaring of the balloon expanded portion 3 of the composite stent so that the proximal end of the stent graft 7 is firmly received within the fenestration 41 of the main graft 33.

Preferably the balloon 62 used to hold the composite stent in place while the flaring takes place is a non-compliant balloon so that excess force is not placed on the composite stent graft and the balloon 64 is of a compliant nature so that it can expand enough to flare the end 7 against the inner wall of the main graft 33.

It will be realised that the relative lengths of the balloon expandable portion and the self expanding portion can be varied depending upon the size of the aneurysm to be treated, the desired extension of the more rigid section into the side branch artery and the morphology of the side branch vessel.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

The invention claimed is:

1. A stent graft configured for placement into a fenestration of a previously placed main stent graft, the stent graft comprising a tubular body of biocompatible graft material having a first end, a second end, a first end edge, a lumen therethrough, an inside, an outside, a balloon radially expandable stent having a tubular portion disposed adjacent the first end of the tubular body and extending along the tubular body toward the second end and having a selected diameter and a flareable extension portion extending longitudinally beyond the first end edge of the tubular body such that the extension portion of the balloon expandable stent is expandable radially beyond the selected diameter of the tubular body, a plurality of discrete self radially expanding stents spaced apart on the tubular body and positioned on the tubular body and extending from the balloon radially expandable stent to the second end of the tubular body, wherein the balloon radially expandable stent comprises a series of interconnected rings.

2. The stent graft of claim 1, wherein the tubular portion of the balloon expandable stent extends from about the middle of the side branch graft to the first end edge of the side branch graft.

3. The stent graft of claim 2, wherein the plurality of discrete self radially expanding stents includes a terminal self-expanding stent at the second end of the tubular body and inside the tubular body.

4. The stent graft of claim 2, wherein a first of the plurality of discrete self radially expanding stents is disposed directly adjacent an end of the tubular portion of the balloon expandable stent.

5. The stent graft of claim 4, wherein the plurality of discrete self radially expanding stents extends to the second end of the tubular body.

6. The stent graft of claim 3, wherein a plurality of the plurality of discrete self radially expanding stents is disposed on an exterior of the stent graft.

7. A stent graft configured for placement into a fenestration of a previously placed main stent graft, the stent graft comprising a tubular body of biocompatible graft material having a first end, a second end, a first end edge, a lumen therethrough, an inside, an outside, a balloon radially flareable extension portion at the first end and extending beyond the first end edge, a tubular balloon expandable stent portion having a first rigidity connected to the balloon radially flareable portion and extending along a length of the tubular body toward the second end, a self-expanding tubular stent portion disposed adjacent the tubular balloon expandable stent portion and extending to the second end and having a second rigidity less than the first rigidity, wherein the tubular balloon expandable stent portion and the self-expanding tubular stent portion have a selected diameter and the balloon radially flareable extension portion is expandable radially beyond the selected diameter of the tubular body, wherein the balloon radially expandable stent portion comprises a series of interconnected rings, wherein the balloon radially expandable stent portion and the self-expanding tubular stent portion are covered by the tubular graft body and the balloon radially flareable extension portion is free of any covering.

8. The stent graft of claim 7, wherein the balloon radially expandable stent portion is disposed within the tubular graft body.

9. The stent graft of claim 7, wherein the balloon radially expandable stent portion and the self-expanding stent portion are disposed on an outside of the tubular graft body.

10. The stent graft of claim 7, wherein the balloon radially expandable stent portion and the self-expanding stent portion are disposed on an inside of the tubular graft body.

\* \* \* \* \*